United States Patent [19]
Dobbs

[11] Patent Number: 6,148,058
[45] Date of Patent: Nov. 14, 2000

[54] SYSTEM AND METHOD FOR REAL TIME MEASUREMENT OF DETECTOR OFFSET IN ROTATING-PATIENT CT SCANNER

[75] Inventor: John M. Dobbs, Hamilton, Mass.

[73] Assignee: Analogic Corporation, Peabody, Mass.

[21] Appl. No.: 09/177,998

[22] Filed: Oct. 23, 1998

[51] Int. Cl.$^7$ ................................................ A61B 6/03
[52] U.S. Cl. ............................ 378/19; 378/10; 378/20; 378/901
[58] Field of Search .................. 378/4, 10, 17, 378/18, 19, 20, 146, 195, 901

[56] References Cited

U.S. PATENT DOCUMENTS

| | | | |
|---|---|---|---|
| 4,048,505 | 9/1977 | Hounsfield | 250/445 |
| 4,176,279 | 11/1979 | Schwierz et al. | 250/445 |
| 4,233,507 | 11/1980 | Volz | 250/252 |
| 4,472,822 | 9/1984 | Swift | 378/10 |
| 4,651,335 | 3/1987 | Kalender et al. | 378/20 |
| 4,710,875 | 12/1987 | Nakajima et al. | . |
| 4,782,502 | 11/1988 | Schulz | 378/18 |
| 4,860,331 | 8/1989 | Williams et al. | 378/163 |
| 4,870,666 | 9/1989 | Lonn et al. | 378/18 |
| 4,961,208 | 10/1990 | Okada | 378/17 |
| 5,034,969 | 7/1991 | Ozaki | 378/18 |
| 5,036,530 | 7/1991 | DiGiovanna et al. | 378/208 |
| 5,109,397 | 4/1992 | Gordon et al. | 378/205 |
| 5,299,253 | 3/1994 | Wessels | 378/163 |
| 5,671,263 | 9/1997 | Ching-Ming | 378/8 |
| 5,680,426 | 10/1997 | Ching-Ming | 378/8 |
| 5,774,519 | 7/1998 | Lindstrom et al. | 378/18 |

*Primary Examiner*—David V. Bruce
*Assistant Examiner*—Drew A. Dunn
*Attorney, Agent, or Firm*—McDermott, Will & Emery

[57] ABSTRACT

A rotating-patient computed tomography scanning system in which the detector offset is measured in real time for each scan. At least one x-ray—absorbent reference structure is disposed in the field of view, so that a projection of the reference structure is present in every view of the patient. The position of the reference structure can be expressed in terms of the detector offset for each view of the patient. The detector offset for a given image can therefore be determined at the time the image data is obtained. The offset value is used in the data obtained from the current scan to reconstruct images that are free of artifacts that are caused by errors in the detector offset.

9 Claims, 3 Drawing Sheets

SYSTEM AND METHOD FOR REAL TIME MEASUREMENT OF DETECTOR OFFSET IN ROTATING-PATIENT CT SCANNER

TECHNICAL FIELD

The present invention relates to computed tomography (CT) scanners in which the patient is rotated relative to a stationary x-ray source and detector array.

BACKGROUND OF THE INVENTION

So-called "rotating patient" computed tomography (CT) scanners are disclosed in, for example, U.S. Pat. Nos. 4,472,822 to Swift, 4,961,208 to Okada, and 5,036,530 to DiGiovanna et al. In such scanners, the patient is positioned in an upright position between an x-ray source and a bank of x-ray detectors, the source and detectors being fixed relative to one another. The patient is rotated through small incremental angles about a vertical rotation axis as x-rays are passed from the source through the patient to the detectors. For any given focal spot and detector position, a view or projection is obtained which provides data about a given two-dimensional slice of the patient's anatomy within a horizontal scan plane. The patient is then rotated to a new angular position for another view in the same horizontal scan plane. After a desired number of views are obtained in a given horizontal scan plane, the x-ray source and detectors are moved together, relative to the patient, along a vertical translation axis to a new horizontal scan plane to obtain image information about the patient in that plane. A series of such horizontal scans may be taken and the data reconstructed to provide an image of the patient's anatomy.

CT scanners generally employ an array of discrete x-ray detectors arranged on an arc of a circle in diametric opposition to the focal spot. For best resolution, it is necessary to use many small detectors, so that the fan beam can be thought of as divided into many equally spaced tiny rays, each ray being detected by a single detector to provide a single intensity measurement for that ray. The distance between the centers of these detectors is referred to as the "period" of the detector array. The period is equal to the detector width plus the width of the space between adjacent detectors. To ensure that the data are sufficiently sampled, it is known to increase the amount of data taken by positioning the detectors so that they are offset by a predetermined amount from, i.e., not centered relative to, a ray extending from the focal spot and passing through the isocenter of the system. The amount of the offset is typically some fraction of the period of the detector array. This offset of the detectors when they are in one position relative to the patient is manifested as an equal and opposite offset when the detectors are on the opposite side of the patient, thereby doubling the amount of data taken within a single 360° scan. A preferred detector offset is typically ¼ or ¾ of the period of the detector array; however, any offset value can be used. Such use of detector offsets is disclosed, for example, in U.S. Pat. No. 4,048,505 to Hounsfield and U.S. Pat. No. 4,176,279 to Schwierz et al.

In a rotating patient scanner, the vertical axis of rotation of the patient will not be exactly parallel to the vertical translation axis along which the x-ray source and detectors move. This is because the detectors in a rotating patient scanner are not fixed with respect to the isocenter of the scanner. In contrast, in CT scanners, in which the patient is held stationary and the x-ray source and detectors rotate about the patient, there is no discernible divergence in the respective rotation and translation axes, because the detectors have a fixed spatial relation to the isocenter of the system. Thus, in the rotating patient scanner, the detector offset will generally vary from scan to scan in proportion to the extent of nonparallelism of the vertical rotation axis of the patient support and the vertical translation axis of the detectors. If not properly handled in the reconstruction algorithm, such a variation in the detector offset from slice to slice may introduce artifacts into the reconstructed image, as the value of the offset for each slice cannot be precisely maintained within a very small error for each scan.

Although the detector offset may be nominally set at a given value, to avoid the introduction of at least some types of image artifacts, it is necessary to determine an actual or true value for the detector offset $\delta$ for a given set of x-ray intensity data. If the true offset $\delta$ is known to within a sufficiently small error, the x-ray intensity data from the detectors can be reconstructed using, for example, back-projection algorithms or other known algorithms, to provide an image which is free of artifacts caused by changes in the detector offset over a significant range of offset values.

Although the prior art discusses rotating patient CT scanners, the problem of variation in the detector offset as a function of axial position of the x-ray source and detectors, intrinsic to rotating-patient CT scanners, is not discussed.

It is known to provide various reference structures of known radiation attenuation characteristics within the image field of a CT scanner in order to provide reference data for x-ray density calibration purposes. Such reference structures are typically placed on or in a patient support table, or within a removable patient overlay or support, so that the reconstructed image contains information about both the patient's anatomy and the reference structures. U.S. Pat. Nos. 5,034,969 to Ozaki, 4,870,666 to Lonn et al., 4,651,335 to Kalender et al., 4,233,507 to Volz and 4,782,502 to Schulz all disclose the use of such reference structures for the purpose of calibration or standardization of the image data.

U.S. Pat. No. 5,109,397 to Gordon et al., assigned to the assignee of the present invention, discloses a rotating gantry CT scanner (i.e., a scanner in which the patient is stationary and the x-ray source and detectors rotate about the patient) which includes an x-ray opaque ring surrounding the patient and disposed entirely within the image field. The ring is thus visible in every view of the patient and provides an indication of lateral movement of the source and detectors for each incremental angular position during a scan. This information is used to adjust the image data to compensate for such movement so as to ensure that the data are accurate for image reconstruction using known back-projection algorithms. However, the ring structure of Gordon et al. is used in a rotating gantry scanner. Thus, the problem of variations in the detector offset due to divergent rotational and translational axes of, respectively, the patient and the detectors, a problem inherent only in rotating patient scanners, does not occur. Gordon et al. does not address or provide a solution to this problem.

U.S. Pat. No. 4,860,331 to Williams et al. discloses an image marker device which includes x-ray—opaque reference structures and is attached to the patient's skin in a desired location. The marker device is used to determine the patient's position relative to an external reference frame. However, as the marker device is relatively small, the reference structures are not necessarily present in every image of the patient, and they are not used to measure detector offset so as to adjust the data in the reconstructed image. Furthermore, Williams et al. do not disclose or refer to the problem of errors in the detector offset, and the resulting introduction of image artifacts.

U.S. Pat. No. 4,710,875 to Nakajima et al. discloses an alignment procedure for a digital radiography system in which x-ray—opaque reference points or lines are recorded together with image data in order to provide an indication of any rotation or shift of the imaged features from scan to scan. The reference points or lines are not visible in every image of the patient. Information about the imaged features cannot therefore be used to adjust the reconstruction data to eliminate artifacts caused by changes in the detector offset. Furthermore, Nakajima et al. do not disclose or refer to the problem of errors in the detector offset, and the resulting introduction of image artifacts.

Thus, it would be advantageous to provide a rotating-patient computed tomography scanner which addresses and overcomes these deficiencies, which are not present, and therefore not addressed, in prior art rotating gantry scanners.

SUMMARY OF THE INVENTION

The present invention is a rotating-patient computed tomography scanner which provides an identifiable, continuous reference structure within the image field which can be seen in all projections of the patient. The actual detector offset for any set of image data within a horizontal scan can be determined from the projections of the reference structure in the image field.

The presence of a reference structure in the image field provides a characteristic pattern in the corrected (but not reconstructed) image data which is easily distinguished from anatomical features, on which the reference structure is superimposed. If the reference structure is a simple object, such as a rod, which is oriented, for example, substantially perpendicular to the scan plane, its image will be a small dot in the image field of any given slice. The data from which a given image is reconstructed comprises a set of projections or views of the object being scanned. If the data from these views are displayed as a two-dimensional plot with the position of the rod shown in each view, the data define a characteristic curve. Each view provides data for an equation of the curve, which will include three unknown variables, i.e., the polar coordinates ($\rho$ and $\alpha$) of the location of the rod and the detector offset $\delta$. For $\eta$ projections there will be $\eta$ equations for the curve which describes the location of the reference structure in each projection. Using standard error minimization techniques, the values of $\rho$, $\alpha$ and $\delta$ can be determined so as to provide the smallest mean square error between the measured values and the values predicted by the equations. Since the values of $\rho$, $\alpha$ and $\delta$ change relatively little with vertical translation of the detectors, they can be computed for one slice and used in the image reconstruction computations for the next slice.

A computed tomography scanning system according to one aspect of the invention includes an x-ray source and a plurality of x-ray detectors cooperatively mounted with the x-ray source so as to intercept a fan beam of x-rays originating at a focal spot of the x-ray source, thereby defining a scan plane and a field of view within the scan plane. A rotatable platform is disposed between the x-ray source and the detectors and is adapted to support a patient for rotation about a substantially vertical rotation axis. A translation element moves the x-ray source and detectors together relative to the patient along a substantially vertical translation axis. A data acquisition system (DAS) acquires x-ray intensity data from the detectors and reconstructs an image from the data. The detectors are offset relative to a central ray extending from the focal spot through the rotation axis by a predetermined amount.

The scanning system of the invention further includes at least one x-ray absorbent reference structure which is disposed within the field of view of the scanner and extending transverse to the scan plane. It provides at least one data point in each projection of the patient and in at least one scan of the patient. The data in a given scan define a curve which is characteristic of the structure. The curve is expressed in terms of the position of the reference structure, and a variable for the detector offset. The scanning system further includes means for determining, for each scan and in real time, a true value for the detector offset, and means for using the true offset value to adjust constants used in the image reconstruction process to substantially eliminate artifacts in the reconstructed image which are caused by errors in the detector offset value used in the image reconstruction computation.

In a preferred embodiment, the reference structure extends in a direction which is substantially perpendicular to any given scan plane, so that it is visible in all scans of the patient. The reference structure preferably has a substantially circular cross-section, so that its projection is uniform in substantially all views.

In a preferred embodiment, the reference structure is associated with a patient immobilization structure disposed within the field of view. The patient immobilization structure is adapted to immobilize and maintain a patient in a desired fixed position and orientation relative to the x-ray detectors during a scan.

The patient immobilization structure, in one preferred embodiment, comprises a substantially x-ray transparent framework adapted to surround at least a portion of the patient, and one or more substantially x-ray transparent packing elements adapted to fit within and conform to the region between the framework and the patient so as to immobilize the patient within the framework.

The framework may comprise a unitary structure, or it may comprise two or more complementary sections adapted to fit together around a portion of the patient.

According to another aspect of the invention, there is provided a method for substantially eliminating artifacts in the reconstructed image which are caused by changes in the detector offset, for use in a rotating patient computed tomography scanner as previously described. The method comprises the steps of:

a) providing at least one x-ray absorbent reference structure disposed transverse to the scan plane within the field of view, wherein the projection of the reference structure provides at least one data point in each view of the patient, wherein the data from the reference structure in a given scan define a curve expressed in terms of a variable for the detector offset;

b) determining, for each scan, and in real time, a true detector offset value; and c) using the true detector offset value to adjust the constants of the image reconstruction process to substantially eliminate such artifacts in the reconstructed image.

In a preferred embodiment, the step of determining a true offset value includes the step of fitting the data from each scan to a suitable model and determining values for $\rho$, $\alpha$ and $\delta$ which minimize the mean square error between the measured data and the data predicted from the model.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be made to the following detailed description taken in connection with the accompanying drawings, in which.

Like elements in the respective FIGURES are labeled with like reference numerals.

DETAILED DESCRIPTION OF THE DRAWINGS

Figure 1:
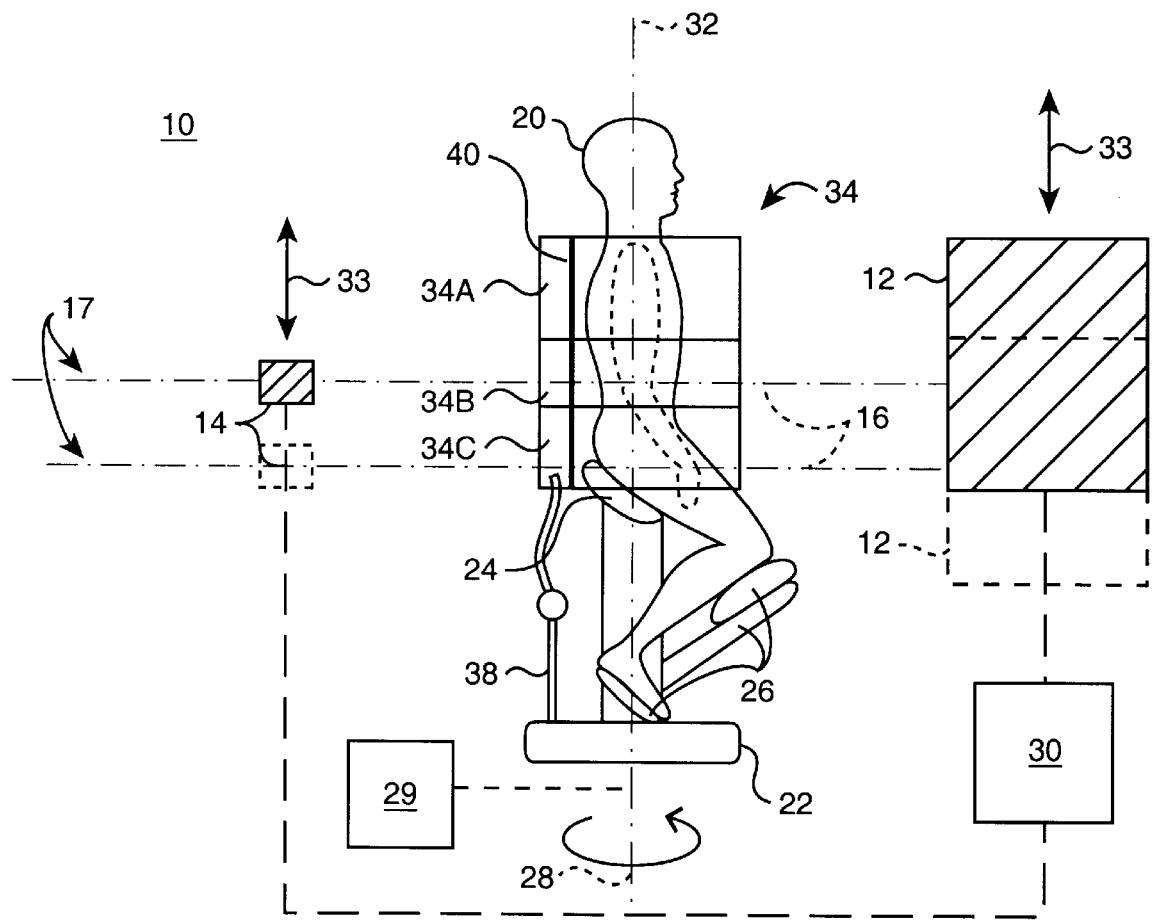
FIG. 1 is a simplified side view of the scanning system of the present invention.
Figure 2:
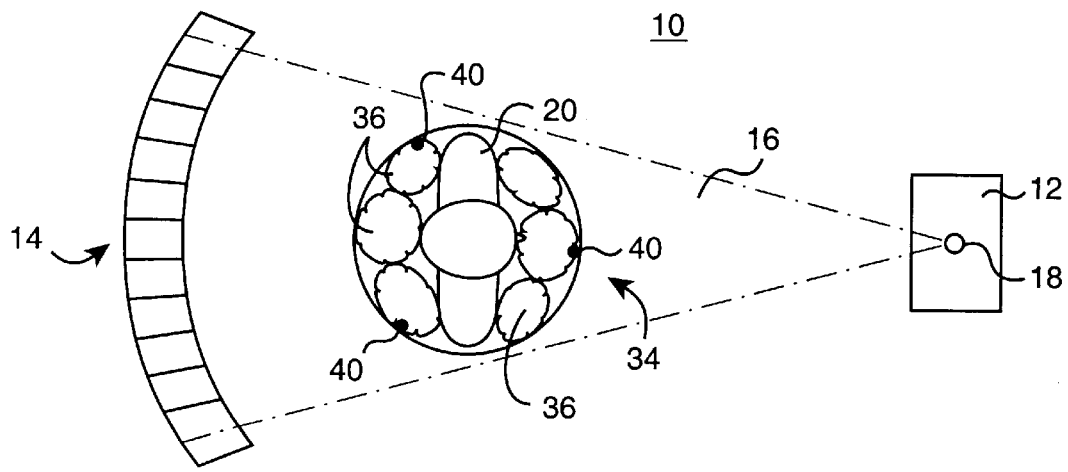
FIG. 2 is a simplified plan view of the scanning system of to the present invention.

FIGS. 1 and 2 illustrate a tomography system according to the invention. The scanning system 10 includes an x-ray source 12 and a plurality of x-ray detectors 14 cooperatively mounted with the x-ray source so as to intercept a fan beam 16 of x-rays originating at a focal spot 18 of the x-ray source. The fan beam 16 defines a fan-shaped field of view in a scan plane 17. The field of view preferably includes all of the patient 20, as well as support members for supporting and immobilizing the patient, as detailed more fully below.

A rotatable platform 22 for the patient 20 is disposed between the x-ray source 12 and the detectors 14. The platform 22 is outfitted with a seat 24 and various supports 26 for the patient to rest on. The rotatable platform 22 supports the patient 20 for rotation about a substantially vertical rotation axis 28 relative to the x-ray source and detectors, which remain stationary with respect to each other. A drive system 29 controls rotation of the platform 22.

The scanning system further includes a drive system 30 for moving the x-ray source 12 and detectors 14 together along a substantially vertical translation axis 32 relative to the patient in the direction of arrows 33. The range of vertical travel of the x-ray source and detectors along the vertical translation axis 32 defines a locus of horizontal scan planes and fan beams which are parallel to scan plane 17 and fan beam 16.

The detector/x-ray source translation axis 32 is approximately coincident with the axis of rotation 28 of the rotatable patient support platform 22. However, the two axes will not coincide exactly because although the detectors and x-ray source are fixed relative to each other, they are not fixed relative to the rotatable platform. As a result of this nonparallelism, errors may be introduced into the x-ray intensity data obtained from the detectors, and thus artifacts may be introduced into the reconstructed image.

The scanning system of the present invention includes means for measuring, in real time and for each scan, a true detector offset, δ. This is accomplished by providing an x-ray absorbent reference structure 40 in the field of view of the scanner. The purpose of the reference structure is to provide, in every view of the patient, a data point representing the reference structure, which has a known location in the image field. Thus, in every scan, which incorporates views of the patient over a full rotation of the patient, there will be a characteristic curve which represents the projection of the reference structure in that scan. This curve can be expressed in terms of the polar coordinates, α and ρ, of the reference structure, and the detector offset, δ. Each view will provide a unique measured location for the data point, and a corresponding calculated location from the expression for the curve, in which these three values are variables. However, because many more than three projections will be obtained in a given scan, there will be many more than three equations for the three unknown variables. Thus, from the equations for the curve in a given scan, the values for the unknown variables can be determined using standard error minimization techniques. The detector offset can thus be determined for any given scan plane, i.e., for any given position of the x-ray detectors relative to a patient.

The reference structure preferably extends transverse to the scan plane and is preferably visible in every possible slice, i.e., in every possible horizontal position of the detectors.

In one embodiment, the reference structure comprises a patient immobilization framework 34 for maintaining the patient 20 in a desired position and orientation relative to the x-ray detectors during a series of scans. The patient immobilization framework 34 preferably is in the form of a substantially x-ray—transparent structure which is adapted to surround and immobilize the patient during and between scans. A suitable x-ray—transparent material for the framework may be, for example, polycarbonate. As shown in the FIGS., the framework may be, for example, in the form of a cylinder which may be of unitary construction or, as shown in FIG. 1, in complementary sections 34A, 34B, 34C, etc. that fit together to provide convenient access for the patient. Other geometric configurations for the framework which adequately surround and immobilize the patient without obstructing anatomical or reference structures are considered to be within the scope of the invention.

To immobilize the patient, the space between the patient 20 and the framework 34 can be filled with a substantially x-ray—transparent packing material 36, such as bags of low-density polymer foam beads, hollow plastic spheres, or the like. The bags of filler material readily conform to the patient's body and to the framework and can be evacuated so as to be made relatively rigid. A vacuum manifold 38 may be provided for this purpose.

The reference structures 40 may be associated with the platform 22, the immobilization framework 34, or even with the patient. They are preferably made of a material which is visible under x-rays, such as aluminum or fiberglass-reinforced plastic, and they are preferably circular in cross-section so that they have a constant profile in all views.

A preferred form for the reference structure is a rod having a circular cross-section, so that its projection is uniform in substantially all views. One or more of such rods can be placed near the patient within the field of view, as shown in FIGS. 1 and 2. Each rod will provide a characteristic pattern in the data obtained over a scan or a significant portion of a scan. In a preferred embodiment, the rod or rods may be associated with the patient immobilization framework 34, as shown in FIGS. 1 and 2, to ensure that they are always within the field of view of the scanner and are always visible in each projection of the patient. The rods may contribute structural strength and rigidity to the immobilization framework and should not interfere with the patient's access into and out of the scanner.

Figure 3B:
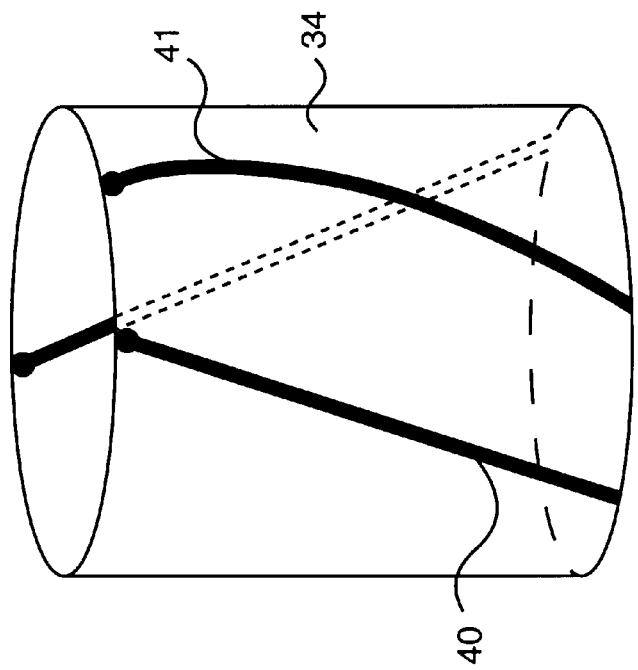
FIGS. 3A and 3B are perspective views of two embodiments of a patient immobilizing structure with at least one reference structure associated therewith.
Figure 3A:
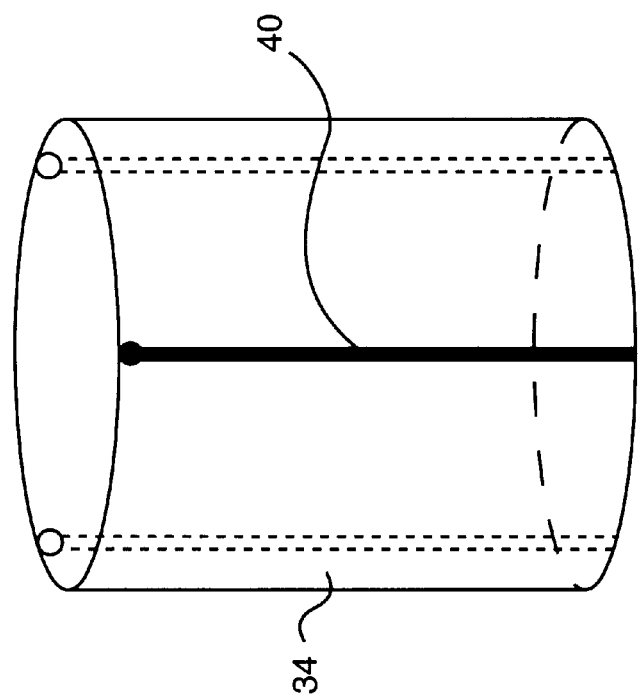

FIGS. 3A–3B illustrate various configurations for a reference structure 40 and an immobilization framework 34, which is shown here as a cylindrical structure. In FIG. 3A the framework includes three reference structures in the form of generally straight rods. The rods can be oriented generally vertically or angled, provided that they are continuous, i.e., not broken or otherwise interrupted, in the vertical direction. The rod or rods preferably extend throughout the entire vertical range of translational movement of the x-ray detectors and source so that they are present in every possible horizontal slice plane of the scanner. Although a single reference structure, such as a rod meeting these requirements, is sufficient, multiple reference structures may be employed to reinforce the framework or to ensure that anatomical features do not obstruct the reference structure in any given view.

One of the rods 41 shown in FIG. 3B is slightly bowed or curved. Such a configuration for the reference structure is also permissible. As long as the reference structure has some vertical component which extends through substantially the full range of vertical travel of the x-ray source and detectors, a portion of at least one of the reference structures will always be visible in each view and in each scan of the patient.

Other configurations of the reference structures and immobilization framework which satisfy these criteria are considered to be within the scope of the invention.

The scanning system also includes means for determining true values for the detector offset, δ. Since each projection provides data about the reference structure, each scan will provide data about the location of the reference structure in the form of a characteristic curve. There will thus be an equation for the projection of the reference structure for each view, expressed in terms of the polar coordinates (ρ,α) of the location of the reference structure in the image field, and the detector offset, δ. In principal, any three of these equations can be solved to determine a value for the detector offset. However, because of the presence of the patient in the scanner and the noise in the data, it is preferred to obtain data from a full rotation, or at least a significant portion of the rotation. The detector offset value can be used in the reconstruction computation in the current or the next scan because the offset changes very little in successive scans.

Figure 4:
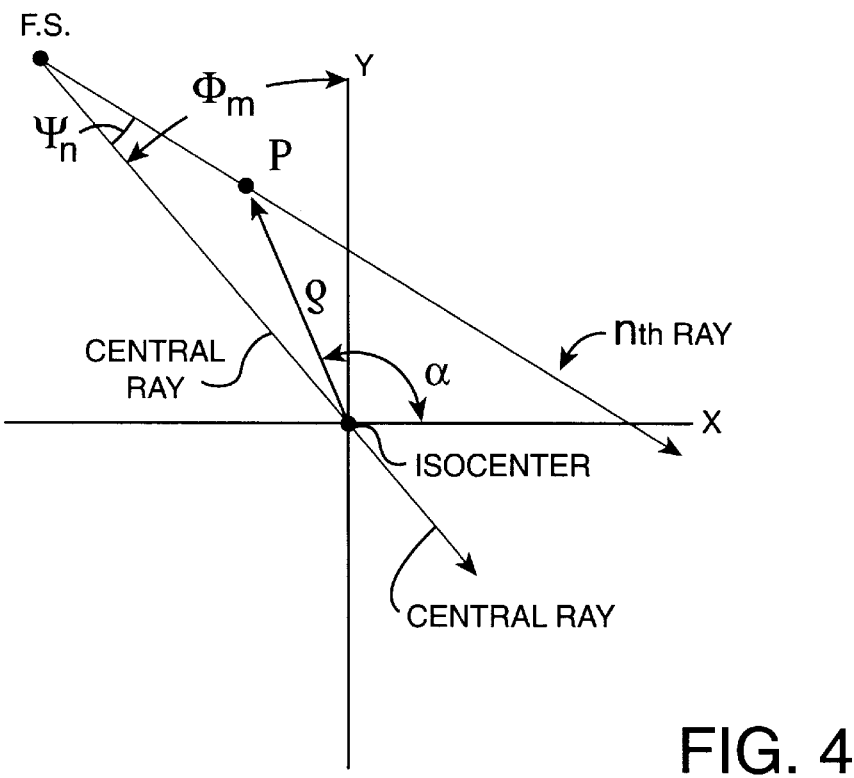
FIG. 4 is a diagram illustrating the coordinates of the projection P of the reference structure in the image field.
Figure 5:
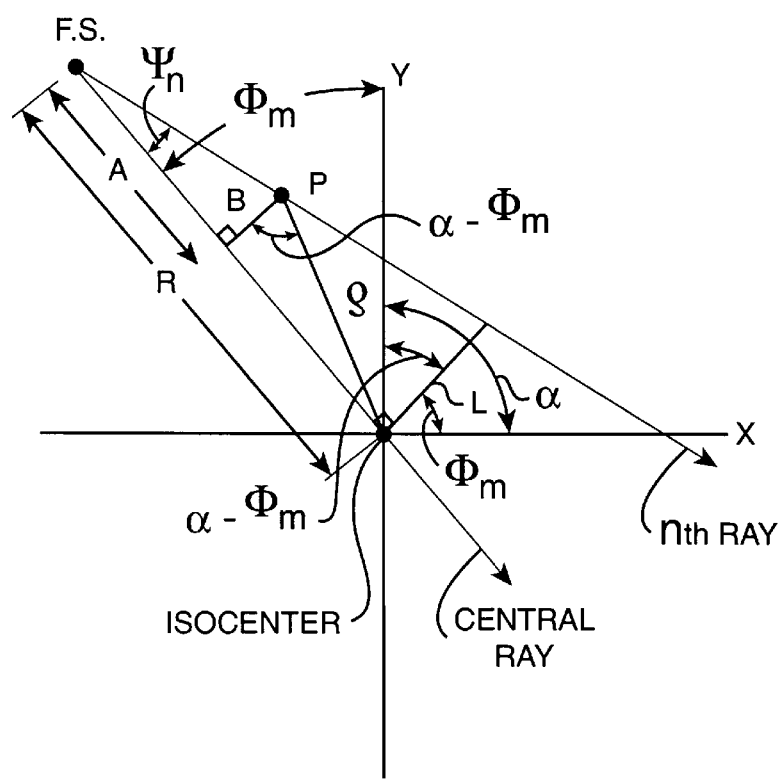
FIG. 5 is a diagram illustrating the relationship of the location of P and the central ray.

FIGS. 4 and 5 illustrate the relationship between the projection of the reference structure, the central ray, and a ray passing through the reference structure in a given view. In FIG. 4, the projection of the reference structure 40, indicated at P, is located at (ρ,α), where ρ is the distance from the isocenter of the system to P, and α is the angle of P relative to the x-axis. The focal spot (FS) is the origin of all fan beam rays. The ray passing from the focal spot through the isocenter of the scanner is the so-called central ray, and this ray makes an angle of $\phi_m$ relative to the y-axis. The ray passing from the focal spot through the projection P is referred to as the nth ray. The angle from a ray passing through a point on one detector to a ray passing through a corresponding point on an adjacent detector (referred to also as the "angular period" of the detector) is $\epsilon$. The detectors of the scanner system are offset by δ, which is a fraction of $\epsilon$ from the center of the most central detector (i.e., the detector for which n=0 and through which the central ray passes). The angle between the central ray and the nth ray is $\psi_n$. Thus, because fan beam rays are equiangularly spaced, $$\psi_n = (n+\delta)\epsilon, \tag{1}$$

where n is an integer such as, for example, 0,±1, ±2, and so on.

FIG. 5 illustrates another relationship between $\psi_n$ and δ. In the graph of FIG. 5, the features of FIG. 4 are reproduced. The distance from the projection P to the central ray is B, and a right triangle is formed with perpendicular legs B and A, as shown. The angle $\psi_n$ is the angle between the central ray and the nth ray, as shown in FIG. 4. Thus, $$\tan\psi_n = \frac{B}{A}. \tag{2}$$

L is a line which is perpendicular to the central ray and parallel to B, and which extends through the isocenter. By inspection, the angle between L and the x-axis is $\phi_m$. The angle between L and ρ is thus $\alpha-\phi_m$, and the angle B and ρ is also $\alpha-\phi$)m. The distance from the focal spot to the isocenter is R.

It is necessary to define $\psi_n$ in terms of δ,α and ρ. Thus, $$B = \rho\cos(\alpha-\phi_m), \tag{3}$$

and $$A = R - \rho\sin(\alpha-\phi_m). \tag{4}$$

Thus, $$\psi_n = (n+\delta)\epsilon = \tan^{-1}\frac{B}{A} = \tan^{-1}\frac{\rho\cos(\alpha-\phi_m)}{R-\rho\sin(\alpha-\phi_m)}. \tag{5}$$

For each of m projections, there will be an equation for A, and the values for ρ, α and δ will be unknown. Because m >>3, there will be more than sufficient information to solve the equations for each of the unknown values. In fact, the problem is vastly overconstrained so that instrumental errors can also be minimized using standard minimization techniques. If the reference structure is substantially perpendicular to the scan plane, the position of the projection of the reference structure will not change significantly in successive scans. Similarly, the value of the detector offset does not change significantly from scan to scan, although over the full range of possible scans the offset may vary enough to introduce artifacts into the reconstructed image which are caused by errors in the detector offset as a function of the vertical translation of the detectors. Thus, by determining the detector offset for each scan, the constants used in the reconstruction algorithms can be adjusted between successive scans so that no image artifacts resulting from detector offset errors are introduced.

Because certain changes may be made in the above apparatus without departing from the scope of the invention herein disclosed, it is intended that all matter contained in the above description or shown in the accompanying drawings shall be interpreted in an illustrative and not a limiting sense.

I claim:

1. In a rotating-patient computed tomography scanning system including an x-ray source, a plurality of x-ray detectors cooperatively mounted with the x-ray source so as to intercept a fan beam of x-rays originating at a focal spot of the x-ray source, thereby defining a scan plane and a field of view within the scan plane, a rotatable platform disposed between the x-ray source and the detectors and adapted to support a patient for rotation about a substantially vertical rotation axis, translation means for moving the x-ray source and detectors together relative to the patient along a substantially vertical translation axis, and a data acquisition system (DAS) for acquiring x-ray intensity data from the detectors and reconstructing an image from the intensity data, wherein the detectors are offset relative to a central ray extending from the focal spot and passing through the rotation axis, means for substantially eliminating artifacts in the reconstructed image which are caused by changes in the detector offset, comprising:

a) at least one x-ray absorbent reference structure disposed transverse to the scan plane within the field of view, wherein the reference structure provides at least one data point in each projection of the patient, wherein the data points in a given scan define a curve expressed in terms of the coordinates of the data point and a variable for the detector offset;

b) means for determining, for each scan and in real time, a true detector offset value; and c) means for using the true detector offset value to adjust constants used in the image reconstruction process to substantially eliminate said artifacts in the reconstructed image.

2. A scanning system according to claim 1, wherein the reference structure extends in a direction which is substantially perpendicular to any given scan plane.

3. A scanning system according to claim 2, wherein the reference structure has a substantially circular cross-section.

4. A scanning system according to claim 3, wherein the reference structure is associated with a patient immobilization structure disposed within the field of view and adapted to immobilize and maintain a patient in a desired position and orientation relative to the x-ray detectors during a scan.

5. A scanning system according to claim 4, wherein the patient immobilization structure comprises a substantially x-ray transparent framework adapted to surround the patient, and one or more substantially x-ray transparent packing elements adapted to fit within and conform to the region between the framework and the patient to immobilize the patient within the framework.

6. A scanning system according to claim 5, wherein the framework comprises a unitary structure.

7. A scanning system according to claim 5, wherein the framework comprises two or more complementary sections.

8. In a rotating-patient computed tomography system, including an x-ray source, a plurality of x-ray detectors cooperatively mounted with the x-ray source so as to intercept a fan beam of x-rays originating at a focal spot of the x-ray source, thereby defining a scan plane and a field of view within the scan plane, a rotatable platform disposed between the x-ray source and the detectors and adapted to support a patient for rotation about a substantially vertical rotation axis, translation means for moving the x-ray source and detectors together relative to the patient along a substantially vertical translation axis, and a data acquisition system (DAS) for acquiring image data and reconstructing an image from the image data, wherein the detectors are offset relative to a central ray extending from the focal spot and passing through the rotation axis, a method of substantially eliminating from the reconstructed image those artifacts caused by changes in the detector offset as a function of vertical translation of the detectors, the method comprising the steps of:

a) providing at least one x-ray absorbent reference structure disposed transverse to the scan plane within the field of view, wherein the reference structure provides at least one data point in each projection of the patient, wherein the data from a given scan define a curve expressed in terms of a variable for the detector offset;

b) determining, for each scan, and in real time, a true detector offset value; and c) using the true detector offset value to adjust the constants of the image reconstruction process to substantially eliminate said artifacts in the reconstructed image.

9. A method according to claim 8, wherein the step of determining a true detector offset value includes the step of fitting the data from each scan to a suitable model and determining values for $\rho$, $\alpha$ and $\delta$ which minimize the mean square error between the measured data and the data predicted from the model.

\* \* \* \* \*